(12) United States Patent
Sun et al.

(10) Patent No.: US 12,357,657 B2
(45) Date of Patent: Jul. 15, 2025

(54) SILVER-/GOLD-COMPOUNDS AND METHODS THEREOF

(71) Applicant: THE UNIVERSITY OF HONG KONG, Hong Kong (HK)

(72) Inventors: Hongzhe Sun, Hong Kong (HK); Pak Leung Ho, Hong Kong (HK); Runming Wang, Hong Kong (HK); Hongyan Li, Hong Kong (HK); Qi Zhang, Hong Kong (HK)

(73) Assignee: THE UNIVERSITY OF HONG KONG, Hong Kong (HK)

( * ) Notice: Subject to any disclaimer, the term of this patent is extended or adjusted under 35 U.S.C. 154(b) by 635 days.

(21) Appl. No.: 17/632,242

(22) PCT Filed: Aug. 21, 2020

(86) PCT No.: PCT/CN2020/110444
§ 371 (c)(1),
(2) Date: Feb. 2, 2022

(87) PCT Pub. No.: WO2021/036923
PCT Pub. Date: Mar. 4, 2021

(65) Prior Publication Data
US 2022/0296639 A1    Sep. 22, 2022

Related U.S. Application Data

(60) Provisional application No. 62/890,667, filed on Aug. 23, 2019.

(51) Int. Cl.
| | |
|---|---|
| *A61K 33/242* | (2019.01) |
| *A61K 31/28* | (2006.01) |
| *A61K 31/555* | (2006.01) |
| *A61K 31/66* | (2006.01) |
| *A61K 31/7135* | (2006.01) |
| *A61K 38/12* | (2006.01) |
| *A61P 31/04* | (2006.01) |

(52) U.S. Cl.
CPC .......... *A61K 33/242* (2019.01); *A61K 31/28* (2013.01); *A61K 31/555* (2013.01); *A61K 31/66* (2013.01); *A61K 31/7135* (2013.01); *A61K 38/12* (2013.01); *A61P 31/04* (2018.01)

(58) Field of Classification Search
CPC .... A61K 33/242; A61K 31/28; A61K 31/555; A61K 31/66; A61K 31/7135; A61K 38/12; A61K 33/38; A61P 31/04
See application file for complete search history.

(56) References Cited

U.S. PATENT DOCUMENTS

2010/0028334 A1*  2/2010  Cottarel ................. A61K 31/16
                                              514/3.3
2019/0099500 A1*  4/2019  Hauser ................... A61K 47/10

FOREIGN PATENT DOCUMENTS

CN          106729611          5/2017

OTHER PUBLICATIONS

Smekalova, et al. "Enhanced antibacterial effect of antibiotics in combination with silver nanoparticles against animal pathogens" The Veterinary Journal, vol. 209, Dec. 31, 2016 (Dec. 31, 2016), pp. 174-179.
Sun, et al. "Rapid antimicrobial susceptibility test for identification of new therapeutics and drug combinations against multidrug-resistant bacteria" Emerging Microbes & Infections, vol. 5, Jan. 25, 2019 (Jan. 25, 2019), pp. 1-11.
International Search Report and Written Opinion for International Application No. PCT/CN2020/110444 mailed on Nov. 25, 2020, 10 pages.
Chinese Office Action for Chinese Patent Application No. 202080059304.9 mailed Mar. 12, 2023.

* cited by examiner

*Primary Examiner* — Robert A Wax
*Assistant Examiner* — Quanglong N Truong
(74) *Attorney, Agent, or Firm* — Amin, Turocy & Watson, LLP

(57) ABSTRACT

Disclosed are pharmaceutical compositions containing (a) polymyxin antibiotic and (b) a mobile colistin resistant proteins (MCRs) inhibitor. The inhibitor relates to silver/gold-compounds or the pharmaceutically acceptable salts thereof. Also disclosed are methods of making silver/gold-compounds or the pharmaceutically acceptable salts thereof and methods for treating MCR-producing bacterial infection via multiple mechanisms.

9 Claims, 10 Drawing Sheets

Silver sulfadizine.

Auranofin

Chloro(triethylphosphine) gold(I)

Aurothiomalate

Aurothioglucose

Aurothiosulfate

SILVER-/GOLD-COMPOUNDS AND METHODS THEREOF

TECHNICAL FIELD

Disclosed are pharmaceutical compositions, methods for treating a mobile colistin resistant proteins inhibitor producing bacterial infection, methods for modulating mobile colistin resistant proteins inhibitor activity, and methods of making pharmaceutical compositions.

BACKGROUND

Since the clinical introduction of penicillin in the 1940s, antimicrobial resistance (AMR) has been always the worldwide crisis. Currently, the colistin, a polymixin E family antibiotic, is regarded as the last-line antibiotic against extensively drug resistant (XDR) gram-negative bacterial infections. Although the phosphoethanolamine (pEtN) transferases in bacteria can catalyze the addition of phosphoethanolamine to lipid A and then induce colistin resistance by weakening the electrostatic interaction between positive charged colistin and negative charged cytomembrane, their genic transmission speeds are limited due to the chromosome-mediation. In 2015, a pEtN transferase gene, called mobile colistin resistance gene (mcr), was firstly identified as plasmid-mediation, resulting in highly transmissible resistance to colistin. The first mcr-gene-encoded transmembrane pEtN transferase is denoted as MCR-1, and can be assigned as a member of alkaline phosphatase (AP) metalloenzymes superfamily due to its structural similarity. Crystallographic studies revealed that cofactor $Zn^{2+}$ interacts with $Glu_{246}$, $Asp_{465}$, $His_{466}$ and phosphorylated $Thr_{285}$ with a tetrahedral geometry, and thus contributing to the desensitization of bacterial pathogens from colistin-sensitive (minimal inhibitory concentration (MIC) of colistin: 0.25-1 μg $mL^{-1}$) to colistin-resistant (MIC of colistin: 4-32 μg $mL^{-1}$) according to the EUCAST. Its rapid transmission enables the co-existence of mcr-1 with other drug resistant genes among/across superbugs. More seriously, recent reports discovered the molecular evolution of mcr genes among various bacterial species found in human, animal and other environment samples. With limited new antimicrobial agents being developed, the generation of MCR and its variants further aggravates the crisis, which forces us to put forward alternative strategies.

Combination therapy comprising an available antibiotic and a non-antibiotic partner has been considered as a more economical and effective alternative to multiple antibiotics treatment and development of monotherapy of new antibiotics. The combination therapies are currently frequently used in clinical therapy regimens, represented by the treatment of infections caused by serine-β-lactamases (SBLs)-producing superbugs with Zavicefta® (ceftazidime and avibactam combination).

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Rather, the sole purpose of this summary is to present some concepts of the invention in a simplified form as a prelude to the more detailed description that is presented hereinafter.

Disclosed herein are pharmaceutical compositions comprising: (a) polymyxin antibiotic and (b) a mobile colistin resistant proteins (MCRs) inhibitor. In one embodiment, the inhibitor relates to silver/gold-compounds or the pharmaceutically acceptable salts thereof. Also provided are methods for preventing or treating MCR-producing bacterial infection. The present disclosure also provides methods of making the composition that comprises the polymyxin antibiotic and the MCR inhibitor. The disclosure also relates to the modulation of MCR activity by silver/gold compounds. The MCRs inhibitor modulates MCRs activity via multiple mechanisms including metal displacement, interference with substrate binding and enhanced rigidity of several vital amino acids. In certain embodiments, the disclosed composition comprises a compound that is a broad-spectrum anti-bacterial agent for treating topical, local and/or systemic bacterial infections. In certain embodiments, the disclosed compound is used in the treatment of infections caused by MCR-producing bacterial pathogens.

To the accomplishment of the foregoing and related ends, the invention comprises the features hereinafter fully described and particularly pointed out in the claims. The following description and the annexed drawings set forth in detail certain illustrative aspects and implementations of the invention. These are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION

Figure 1:
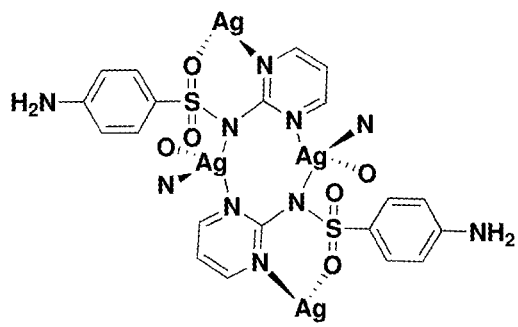
FIG. 1 shows chemical structures of exemplary silver/gold compounds, including silver sulfadiazine, auranofin, chloro(triethylphosphine) gold(I) (Au(PEt$_3$)Cl), aurothioglucose, aurothiosulfate and aurothiomalate.
Figure 1:
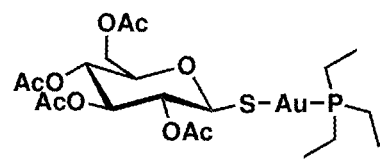
Figure 1:
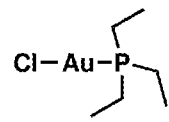
Figure 1:
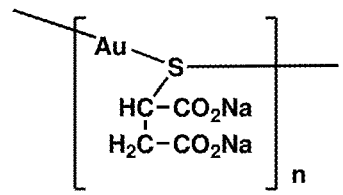
Figure 1:
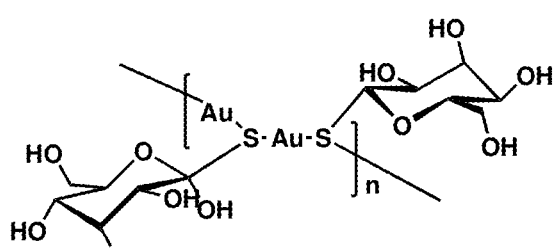
Figure 1:
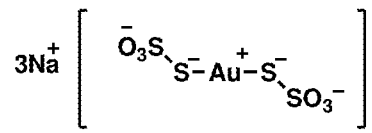

Disclosed herein are pharmaceutical compositions comprising: (a) polymyxin antibiotic and (b) a mobile colistin resistant proteins (MCRs) inhibitor. In one embodiment, the inhibitor relates to silver/gold-compounds or the pharmaceutically acceptable salts thereof. Also provided are methods for preventing or treating MCR-producing bacterial infection. The present disclosure also provides methods of making the composition that comprises the polymyxin antibiotic and the MCR inhibitor. The disclosure also relates to the modulation of MCR activity by silver/gold compounds. The MCRs inhibitor modulates MCRs activity via multiple mechanisms including metal displacement, interference with substrate binding and enhanced rigidity of several vital amino acids. In certain embodiments, the disclosed composition comprises a compound that exhibited anti-resistant ability to slow down the development of MCR resistance in MCR-producing bacteria. In certain embodiments, the disclosed composition comprises a compound that is a broad-spectrum anti-bacterial agent for treating local and/or systemic bacterial infections. In certain embodiments, the disclosed compound is used in the treatment of infections caused by MCR-producing bacterial pathogens.

Provided herein are compositions comprising: (a) a polymyxin antibiotic and (b) an MCRs inhibitor. The inhibitor relates to silver/gold-compounds or the pharmaceutically acceptable salts thereof. The MCR inhibitors serve to modulate the activity of MCRs via multiple mechanisms. In addition, MCRs inhibitors are efficient polymyxin antibiotic partners for the treatment of infections by MCR-producing bacterial pathogens.

In certain embodiments, infections that are treated by the disclosed composition are caused by bacteria that are resistant to polymyxin antibiotics. Polymyxins or polymyxin antibiotics are polypeptide antibiotics. Examples of polymyxins include, but are not limited to Polymyxins B (such as Polymyxins B1 Polymyxins B2) and Polymyxins E (such as Colistin A and Colistin B). In certain embodiments, the polymyxin antibiotics have the following structure:

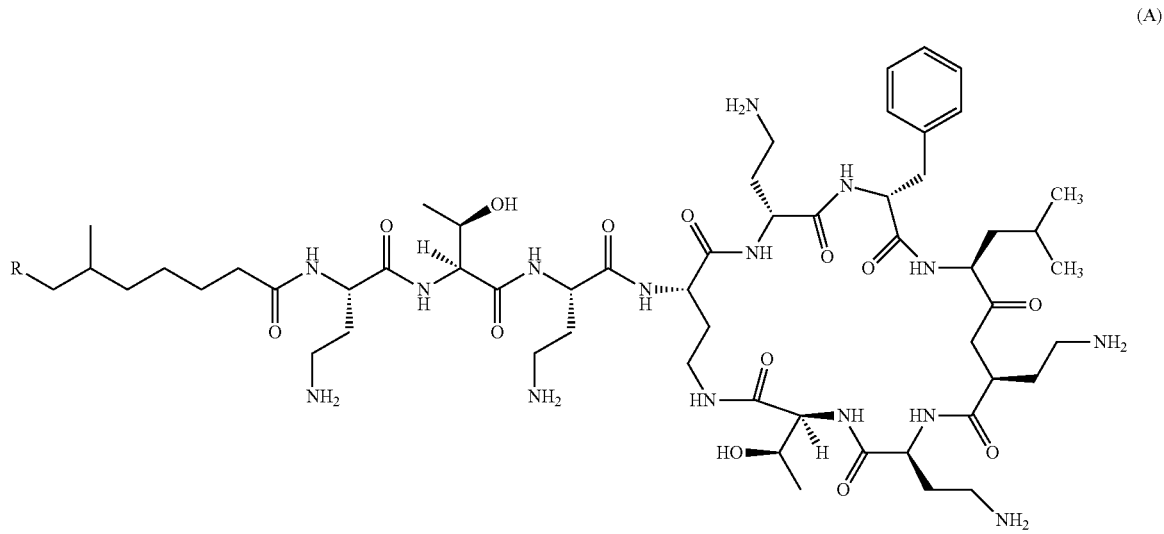

(A)

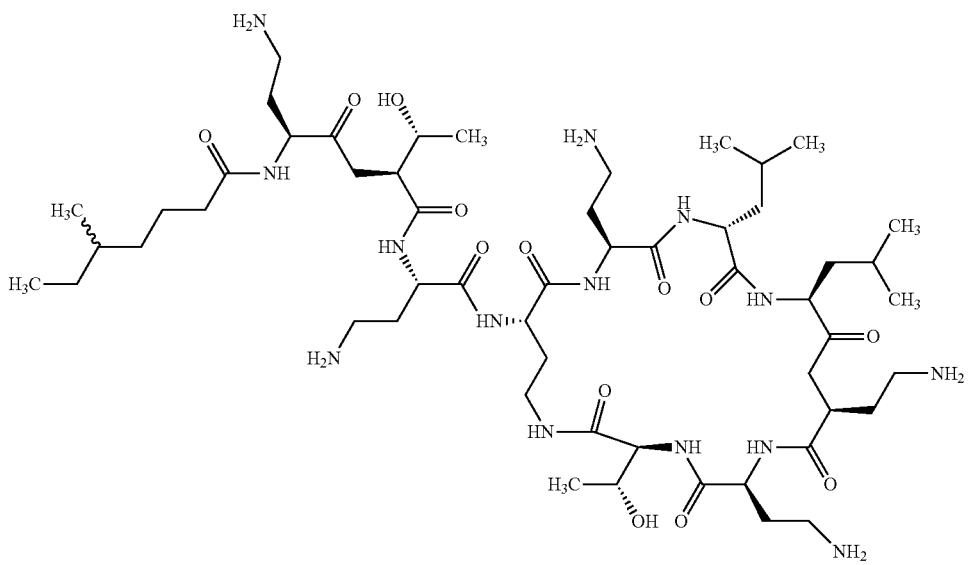 [SMILES: CCC(C)CCCC(=O)N[C@@H](CCN)C(=O)C[C@H](C(=O)N[C@@H](CCN)C(=O)N[C@H]1CCNC(=O)[C@H]([C@@H](C)O)NC(=O)[C@H](CCN)NC(=O)[C@H](CCN)CC(=O)[C@H](CC(C)C)NC(=O)[C@@H](CC(C)C)NC(=O)[C@H](CCN)NC1=O)[C@@H](C)O]

The polymyxin structure: (A) Polymyxin B: R═H is polymyxin B1; R═CH$_3$ is polymyxin B2 (B) Polymyxin E (Colistin).

In certain embodiments, the bacteria are gram-negative, including but not limited to *Salmonella typhimurium, Shigella flexneri, Klebsiella pneumoniae, Escherichia coli, Enterobacter aerogenes, Enterobacter asburiae, Enterobacter kobei*. In certain embodiments, these gram-negative bacteria producing MCRs. In certain embodiments, the MCR-1 variants include MCR-1.1, MCR-1.5, MCR-1.6, MCR-1.7, MCR-1.9, and MCR-1.10. In certain embodiments, the MCR variants included MCR-2.1, MCR-3.1, MCR-4.1, MCR-5.1, MCR-6.1, MCR-7.1

Provided herein are composition comprising a silver-/gold-compound or the pharmaceutically acceptable salts thereof. In certain embodiments, the silver compound is a (a) silver(I) compound or (b) silver nanoparticle. In certain embodiments, silver(I) complex includes but not limited to silver nitrate (AgNO$_3$) and sulfadiazine silver. In certain embodiments, the silver nanoparticle includes commercialized silver nanoparticles (AgNPs) with different nano-sizes (10 nm, 40 nm, 100 nm). In certain embodiments, the gold compound includes (a) a gold(I) compound or (b) gold nanoparticle. In certain embodiments, the gold(I) compound includes but not limited to auranofin, gold(I) chloride (AuCl), aurothioglucose, aurothiosulfate, chloro(triethylphosphine) gold(I) (Au(PEt)$_3$Cl), and aurothiomalate. In certain embodiments, the gold nanoparticle includes commercialized nano-gold particles with different nano-sizes (20 nm, 40 nm, 100 nm).

In another embodiment, the silver nanoparticles and/or gold nanoparticles have various sizes ranging from 3 nm to 250 nm. In yet another embodiment, the silver nanoparticles and/or gold nanoparticles have various sizes ranging from 5 nm to 200 nm.

Also provided herein are methods of using silver/gold compounds for the modulation of MCR activity. In certain embodiments, the MCR inhibitor modulates MCRs activity via multiple mechanisms including metal displacement, interference with substrate binding and enhanced rigidity of several vital amino acids. Provided herein is a method of treating bacterial infections. Provided herein is a pharmaceutical composition comprising: (a) a polymyxin antibiotic and (b) an MCRs inhibitor, as a medicament for the treatment of the MCR-producing bacterial infections. The composition described herein also exhibited anti-resistant ability to slow down the development of MCR resistance in MCR-producing bacteria.

DEFINITIONS

The term "antibiotic" herein refers to compounds that either kill or inhibit the growth of bacteria, and the term "antimicrobial" herein refers to compounds that either kill or inhibit the growth of microorganism, including virus. The term "resistance" and "develop resistance" when refer to a lost ability of compound to reduce the bacterial growth or prevent any increase in bacterial growth. The term "antimicrobial resistance (AMR)" or "antibiotic resistance" herein refers to the ability of a microbe or bacteria to resist these compounds that once could successfully treat the infection caused by them individually.

The "colistin" herein belongs to the polymyxin E family antibiotics which has an extended-broad-spectrum antibacterial activity against a wide variety of gram-negative bacteria and been characterized as the last-line antibiotic. It contains lots of amino group and thus turns to be positive charged in certain pH environment. It can bind to LPS by electrostatic interaction and then release key cell components by increasing membrane permeability and result in bacterial death due to osmotic instability or autolysis. In this embodiment, the structure of colistin is represented by the following formula:

The term "MCR-1" herein refers to a type of phosphoethanolamine (pEtN) transferase, produced by bacteria endowing them to catalyze the phosphoethanolamine transfer to lipid A and then weaken the member positive charge to resist polymyxin E family antibiotic colistin. The term "mcr-1" herein refers to its DNA gene which can be transferred into the mRNA and then translated into MCR-1 protein. The term "MCR-1 variants" herein refers to a member of a set of highly similar proteins that originate from a single gene or gene family of mcr-1. The term "other MCRs" herein refers to a member of a set of highly similar proteins that originate from a single gene or gene family of mcr. The term "MCR-producing bacteria", "MCR-1 producing bacteria" or "mcr genes carrying bacteria" refer to the bacteria that produce MCR-1 or MCR family protein naturally or by the inducement of molecular biology reagent, such as isopropyl B-D-1-thiogalactopyranoside (IPTG).

The term "combination therapy" refers to a therapy that uses more than one medication or modality, typically, these terms refer to using multiple therapies to treat a single disease, and often all the therapies are pharmaceutical. Corresponding, the term "monotherapy" refers to any therapy that uses only one medication.

The term "inhibitor" described herein refers to the molecule which can bind to an enzyme and hinder the enzyme from its catalytic reaction. The term "potentiator" described herein refers to the drug, herb, or chemical which can intensify the effect of a given antibiotic, like colistin, to either kill or inhibit the growth of bacteria in bacterial infection.

The term "silver/gold compounds" refers to (1) silver compound including but not limited to $AgNO_3$ and sulfadiazine silver or AgNPs with different sizes (2) gold compound including but not limited to auranofin, AuCl, aurothioglucose, aurothiosulfate, $Au(PEt)_3Cl$, and aurothiomalate or AuNPs with different sizes, and pharmaceutically acceptable salts, acid salts, esters, or hydrates thereof.

The term "synergistic effect" refers to the interaction between two or more compounds or chemicals when the combined effect is larger than the sum of the effects of the individual components.

The term "in vitro" refers to the experimentation carrying out with microorganisms, cells and biological molecules outside their normal biological contexts. The term "in vivo" refers to experimentation using a whole, living organism as opposed to a partial or dead organism, which is most commonly represented by animal studies and clinical trials.

The term "reducing bacterial growth" includes an interference in bacterial cell growth or processing which can be determined by a reduction in cell number, a reduction in cell division.

The term "cytotoxicity" refers to the property of being toxic to cells.

The term "restore activity" refers to the process of invalid or lower effect antibiotic to be valid or effect antibiotic again.

The term "potential active pocket" or "active site" refers to the area where the key enzyme catalytic reaction occurs. The term "substrate" refers to the biochemistry field, which means the substrate is the material upon which an enzyme acts. The term "substrate binding site" refers to the area where the substrate can interact with enzyme.

The term "biochemical methods" refers to those routine experimental techniques used in the field of biochemistry, which herein include molecular cloning, protein expression and purification as well as protein characterization.

The term "molecular cloning" refers to a general method to engineer a desired DNA fragment into a vector which can hold and preserve it as well as direct its self-replication in host cells. The term "protein expression and purification" involves the host cell was stimulated by some small molecules or not to produce enough desired protein for experimental uses and separate it from other unwanted molecules present inside cells to enhance its homogeneity. The term "overexpressed system" or "native system" refers to the case with or without stimulator individually.

The term "protein characterization" or "biophysical properties" refers to these protein properties known by various physical and biochemical techniques, including the structure and function of purified protein.

The term "metal content or metal ratio" refers to the ratio of metal ion(s) to a protein. The term "time-dependent absorbance" and "dose-dependent absorbance" refer to a phenomenon that the absorbances of compounds were determined by the value of a variable representing time or addition doses individually.

The term "clinically relevant susceptible range" refers to the zone of inhibition or MICs at which an organism is considered to be susceptible based on obtainable serum concentrations of the drug, test compounds and clinical trials.

The term "pharmaceutically acceptable salt" refers to any salt(s) of a compound provided herein which retains its biological properties and which is nontoxic and desirable for pharmaceutical use. Such salts may be derived from a variety of organic and inorganic counter-ions well known in the art.

The terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgus monkey, a chimpanzee and a human).

The term "a subject in need thereof" refers to a subject having a bacterial infection, or a subject at risk of developing a bacterial infection. The subject may have been diagnosed as having such a bacterial infection as described herein or using standard medical techniques known to those of skill in the art. Alternatively a subject may exhibit one or more symptoms of bacterial infection.

The terms "therapeutic agent" and "therapeutic agents" refer to any agent(s) that can be used in the treatment or prevention of an infection. In certain embodiments, the term "therapeutic agent" includes a compound provided herein. In one embodiment, a therapeutic agent is an agent that is known to be useful for, or has been or is currently being used for the treatment or prevention of the infection. The terms "compound", "agent" and "drug" are interchangeable.

The term "therapeutically effective amount" includes an amount of a compound or composition that, when administered to a subject for treating an infection, is sufficient to affect such treatment. A "therapeutically effective amount" can vary depending on, inter alia, the compound, the infection and its severity, and the age, weight, etc., of the subject to be treated.

The terms "treating" or "treatment" of any infection refers, in one embodiment, to ameliorating the infection that exists in a subject. In another embodiment, "treating" or "treatment" includes ameliorating at least one physical parameter, which may be indiscernible by the subject. It is intended to include preventing, ameliorating, curing, reducing bacterial growth, or preventing any increase in bacterial growth.

The terms "resistant", "resistance" and "develop resistance" refer to bacteria or bacterial infections that are no longer responsive to a compound or drug that was previously effective in reducing the bacterial growth or preventing any increase in bacterial growth.

The term "about" refers to ±0.5 for a numerical value, or up to 10% for other values/terms.

The term "pharmaceutical composition" refers to a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade).

Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The terms "pharmaceutically acceptable carrier," "pharmaceutically acceptable excipient," "pharmaceutically acceptable diluent," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use.

The term "pharmaceutically acceptable salts" refers to a compound of the present disclosure that can be modified by making acid or base salts thereof. Pharmaceutically acceptable salt refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. Examples of pharmaceutically acceptable salts include, but are not limited to, mineral or organic acid salts of basic residues such as amines; and alkali or organic salts of acidic residues such as carboxylic acids.

The terms "effective amount" and "therapeutically effective amount" as used herein refer to that amount of an embodiment of the composition or pharmaceutical formulation being administered that will relieve to some extent one or more of the symptoms of infection being treated, and/or that amount that will prevent, to some extent, one or more of the symptoms of the infection that the subject being treated has or is at risk of developing.

By "administration" is meant introducing an embodiment of the present disclosure into a subject. Administration can include routes, such as, but not limited to, intravenous, oral, topical, subcutaneous, intraperitoneal, intraarterial, inhalation, vaginal, rectal, nasal, introduction into the cerebrospinal fluid, or instillation into body compartments can be used. A preferred route is oral administration.

acceptable salts thereof. The inhibitor modulates MCRs activity via multiple mechanisms including metal displacement, interference of substrate binding and enhanced rigidity of several vital amino acids.

Provided herein are composition comprising a silver/gold compound or pharmaceutically acceptable salts thereof. In certain embodiments, the silver/gold compound or pharmaceutically acceptable salts thereof include, (1) silver compound including but not limited to $AgNO_3$ and sulfadiazine silver or AgNPs with different sizes (2) gold compound including but not limited to auranofin, AuCl, aurothioglucose, aurothiosulfate, $Au(PEt)_3Cl$, and aurothiomalate or AuNPs with different sizes. In one embodiment, the polymyxin antibiotic and the MCRs inhibitor have a molar ratio ranging from 1:100 to 100:1 by weight (w/w). in another embodiment, the polymyxin antibiotic and the MCRs inhibitor have a molar ratio ranging from 16:1 to 64:1 by weight (w/w). In yet another embodiment, the polymyxin antibiotic and the MCRs inhibitor have a molar ratio ranging from 25:1 to 50:1 by weight (w/w).

In one embodiment, the pharmaceutical compositions herein contain from 0.1% to 99% by weight of at least one polymyxin antibiotic, from 0.01% to 25% by weight of at least one MCRs inhibitor, and optionally from 0% to 99.9% by weight of at least one pharmaceutically acceptable carrier. In another embodiment, the pharmaceutical compositions herein contain from 1% to 95% by weight of at least one polymyxin antibiotic, from 0.1% to 20% by weight of at least one MCRs inhibitor, and optionally from 0% to 99% by weight of at least one pharmaceutically acceptable carrier. In yet another embodiment, the pharmaceutical compositions herein contain from 1% to 90% by weight of at least one polymyxin antibiotic, from 0.5% to 15% by weight of at least one MCRs inhibitor, and optionally from 0% to 90% by weight of at least one pharmaceutically acceptable carrier.

In one embodiment, the polymyxin antibiotic is colistin which has extended broad-spectrum antibacterial activity against a wide variety of bacteria. It contains many amino groups and thus turns to be positive charged in certain pH environment. It can bind to LPS by electrostatic interaction and then releases key cell components by increasing membrane permeability and results in bacterial death due to osmotic instability or autolysis. The structure of colistin is represented by the following formula:

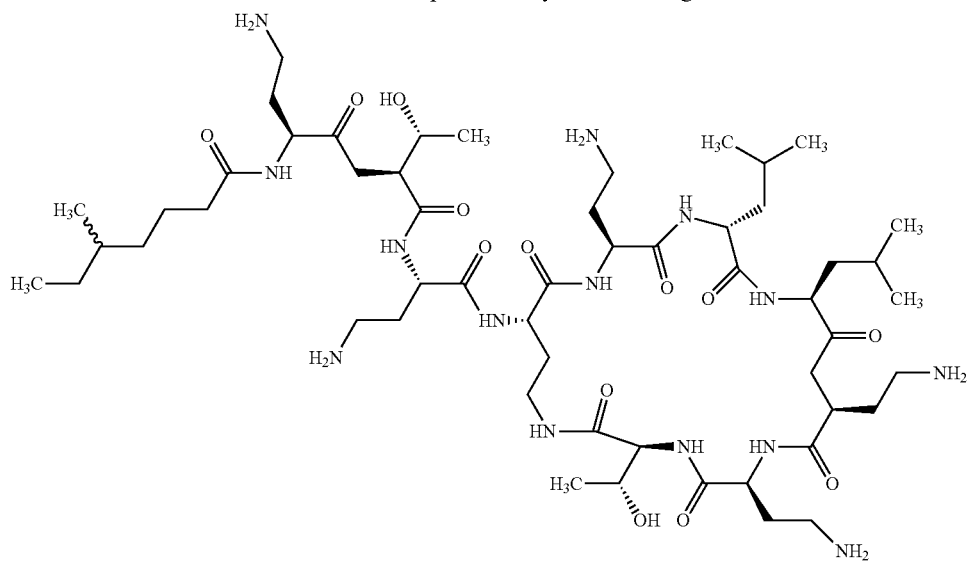

Colistin and its Potentiators

Provided herein is a novel type of wide-spectrum MCRs inhibitor, silver/gold compound or the pharmaceutically The mechanism of action of silver compounds is unveiled by X-ray crystallography. MCR-1 protein crystal was soaked with $AgNO_3$, which showed (a) ten $Ag^+$ ions bound to MCR-1 and one Ag$^+$ replaces one Zn$^{2+}$ cofactor in the potential active pocket. (b) about 60° rotation was observed for vital His$_{395}$ owing to the binding of silver, which may interfere with substrate binding of ethanolamine (ETA) or pEtN to potential active pocket. (c) silver binding aggravated rigidity of vital amino acids including His$_{390}$, Asp$_{465}$, and Glu$_{246}$. Similarly, one Au$^+$ ion was observed in the active pocket of MCR-1 crystal after soaking with auranofin or AuCl.

Combination Therapy

In some embodiments, MCR-producing bacteria showed good restored colistin susceptibility when treated with silver/gold compounds. In certain embodiments, colistin can prevent the bacterial growth or kill them at clinically relevant susceptible range. In one embodiment, the combination of colistin and silver/gold compounds exerts synergistic effect. In one embodiment, the antibacterial efficacy of colistin are increased by 2 to 256 folds as compared to antibiotics that are without the silver/gold compounds or the pharmaceutically acceptable salts thereof as described herein. In another embodiment, the antibacterial efficacy of colistin are increased by 4 to 128 folds as compared to antibiotics that are without the silver/gold compounds or the pharmaceutically acceptable salts thereof as described herein. In yet another embodiment, the antibacterial efficacy of colistin are increased by 8 to 64 folds as compared to antibiotics that are without the silver/gold compounds or the pharmaceutically acceptable salts thereof as described herein. In certain embodiments, either auranofin or silver nitrate was observed to slow down the development of higher-level resistance. Their potential medical use was explored by cell-invaded model for silver nitrate in vitro study.

In one specific embodiment, the clinically relevant susceptible range of colistin towards Enterobacteriaceae is <2 µg mL$^{-1}$ according to the criteria of European Committee on Antimicrobial Susceptibility Testing (EUCAST). In some specific embodiments, the synergistic effect or part synergistic effect is quantified by the calculation of fractional inhibitory concentration index (FICI).

In some embodiments, examples of mcr-1, mcr-1 variants or other mcr genes positive bacteria include, but not limited to *Salmonella typhimurium*, *Shigella flexneri*, *Klebsiella pneumoniae*, *Escherichia coli*, *Enterobacter aerogenes*, *Enterobacter asburiae*, *Enterobacter kobei*. In one embodiment, cell-associated model was established with human hepatoma HepG2 cell line to examine the antimicrobial performance of combination of colistin and AgNO$_3$ or AgNPs against MCR-1-producing bacteria.

EXAMPLES

The following examples illustrate the subject invention. Unless otherwise indicated in the following examples and elsewhere in the specification and claims, all parts and percentages are by weight, all temperatures are in degrees Centigrade, and pressure is at or near atmospheric pressure.

Example 1: Crystallographic Studies of Silver/Gold Binding to MCR-1

Plasmids Construction for Wild-Type Mcr-1, Mcr-1 Variants, Other Mcr Genes, and the Mutated and Truncated Mcr-1 Forms The primary plasmid encoding full length MCR-1 and solvable truncated part (200-541aa) were collected from Dr. Pak Leung Ho's group (HKU) and Prof Hao Quan group (HKU) individually. These primary genes were sub-cloned into pCR-XL-TOPO and pET-15b vectors via the SacI/BamHI and NdeI/BamHI restriction sites individually. All following modified plasmids were constructed from the primary plasmids as PCR template. Point mutations were introduced into the mcr-1 gene by using the QuickChange (Stratagene) commercial kit and confirmed by DNA sequencing (BGI, China). PCR was performed using KOD Hot Start DNA Polymerase (Novagen) based on the reaction conditions described in the protocols by the manufacturers. All restriction enzymes and T4 ligase were from New England Biolab. Both gel extraction kit and plasmids extract kit were purchased from QIAGEN.

Protein expression of MCR-1-S and apo-MCR-1-S Plasmids with mutated or truncated mcr-1 gene were transformed into *E. coli* BL21(DE3). Single colony was picked and inoculated into LB medium supplied with 100 µg mL$^{-1}$ ampicilin and grown at 37° C. overnight. Overnight cultures were amplified 1:1000 into 3 L of LB medium supplemented with 100 µg mL$^{-1}$ ampicilin. After 2.5-hour incubation, 0.2 mM IPTG (isopropy-β-D-thiogalactoside, Sigma-Aldrich, USA) was added into bacterial culture with OD$_{600}$ reading of 0.6~0.8, followed by shaking at 25° C. overnight. These cultured cells were harvested by centrifugation at 4500×g for 30 minutes at 4° C., re-suspended by lysis buffer (20 mM HEPES, PH=7.4, 50 mM NaCl and 20 mM imidazole), lysed by sonication and then centrifuged at 35,000 g at 4° C. for 45 minutes to remove the majority of cell debris. The supernatant was filtered using Minisart syringe filter (0.45 µm) to remove other insoluble cell debris, and applied to a 5 ml Ni(II)-loaded HiTrap chelating columns (GE Healthcare) at a rate of 2 mL min$^{-1}$. The column was washed using five column-volumes of washing buffer (20 mM HEPES, 0.5 M NaCl, and 30 mM imidazole at pH 7.4). The protein was eluted by the same buffer with gradient amounts of imidazole, and was subsequently mixed with 50 NIH units of thrombin (Sigma-Aldrich, USA) and dialyzed in the cleavage buffer (20 mM HEPES, PH=7.4, 10 mM NaCl) at 4° C. overnight. The protein was re-loaded onto another Ni(II)-NTA column to collect the flow-through fraction. Q-HP column (GE) was necessary for its further purification, where the protein sample was eluted by using five column-volumes of the cleavage buffer with gradient amounts of NaCl (10-500 mM). These target sample fractions were loaded onto Superdex 75 (GE Healthcare) equilibrated with running buffer (20 mM HEPES, pH=7.4, 50 mM NH$_4$NO$_3$). Target protein with high purity was concentrated (10 KD, Millipore) to 7 mg mL$^{-1}$ for further use.

Fresh purified MCR-1-S and apo-MCR-1-S were loaded onto superdex 75 columns (GE Healthcare) in running buffer (20 mM HEPES, pH=7.4, 50 mM NH$_4$NO$_3$) at a rate of 0.5 mL min$^{-1}$. MCR-1-S incubated with Zn(Ac)$_2$, AgNO$_3$, AuCl or other related compounds were performed in running buffer individually. Their different conformations were explored by FPLC peak either at 38 KDa (monomer) or at 76 KDa (dimer). All assays were performed in triplicate, repeated three times.

Protein Crystallization and Data Analysis

The purified protein was incubated with 50-100 molecular ratios EDTA at 4° C. for 3 hours and then concentrated to 1 mg mL$^{-1}$ to be apo-MCR-1-S. The samples were separated into aliquots after dialysis with storage buffer (20 mM HEPES, 50 mM NH$_4$NO$_3$, at pH 7.4) for long-term storage at −80° C. Crystal screening (sitting drop) was performed by mixing equal volume of protein and reservoir (100 mM KSCN, 30-32% PEG 3350, 100 mM Tris-HNO$_3$, pH 8.0). Crystals of native MCR-1-S appear at 18° C. after two weeks. They generally diffracted with about 1.8 Å resolutions. The crystals were transferred into new well with 32% PEG 3350, 100 mM Tris-HNO$_3$ (pH 8.0), 25% glycerol and 10 mM EDTA for 1 hour. Next, these crystals were washed three times in cryo-protectant solution (32% PEG 3350, PH 8.0, 25% glycerol and 100 mM Tri-HNO$_3$ (pH 8.0)) and soaked with soaking buffer (32% PEG 3350, pH 8.0, 25% glycerol, 100 mM Tri-HNO$_3$ (pH 8.0) and 5 mM AgNO$_3$ (5 mM AuCl or 5 mM auranofin) for 3 hours (1~3 months) in the prevention of light. The crystals were picked up and then flash-frozen into liquid nitrogen. The 14 crystals generally diffracted to resolutions of 1.58-2.03 Å. Eighteen data were collected at BL17U1 at the Shanghai Synchrotron Radiation Facility (SSRF) 20 at the wavelengths of 0.97915 Å. The diffraction data were processed with HKL2000 at SSRF.

Figure 2:
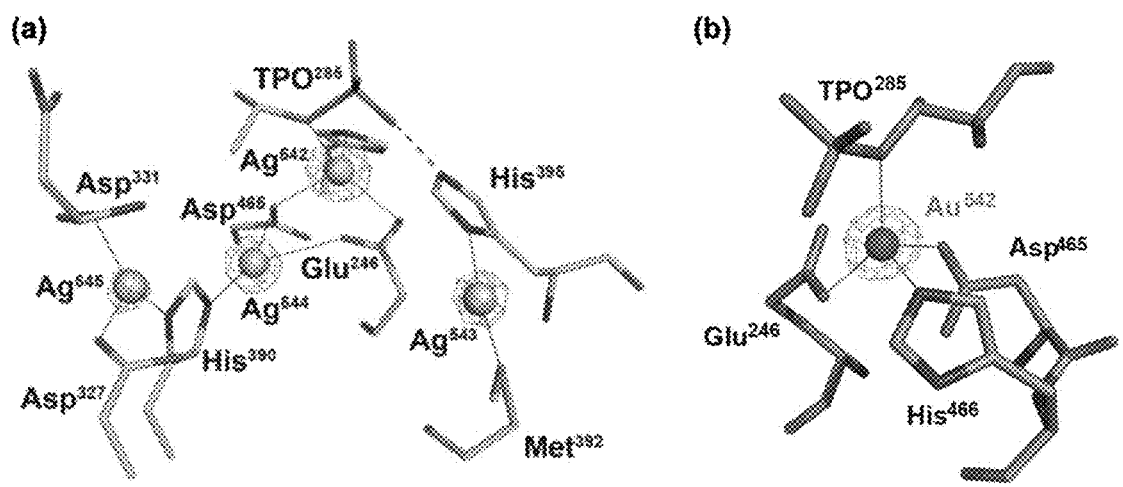
FIG. 2 (a) shows crystallographic analysis of (a) structure of tetra-nuclear silver cluster in the active-site pocket of MCR-1-S enzyme. Ag(I) was shown as wheat spheres are bridged in narrow pocket by either covalent bonds (red solid lines) or hydrogen bond (red dash line), and (b) structure of the active site of Au-MCR-1-S (PDB ID: 6LI6) with the anomalous density peak of Au ion shown as a purple sphere and anomalous density peak of Au in magenta mesh.

Molecular replacement was performed using the program Phaser66 from the CCP4 suite and the $Zn^{2+}$ binding truncated MCR-1 (PDB code: 5GRR) as a searching model. Refinement with the anomalous data and manual rebuilding were done using Refmac67 and Coot68 individually. The Ag(I) and Au(I) occupancy was refined based on atomic B-factor in later stages. Higher $Ag^+$ occupancy (≥0.8) and $Au^+$ occupancy (≥0.45) confirms the replacement of $Zn^{2+}$ after soaking. TLS refinement was incorporated into later refinement processes. Solvents were added automatically in Coot and then manually inspected and modified. The final models were analyzed with MolProbity69. The corresponding Ag-MCR-1-S and Au-MCR-1-S crystals are shown in FIGS. 2 (a) and (b).

Example 2: In Vitro Mechanistic Studies of Enzyme Inhibition

ITC Assay

Figure 3:
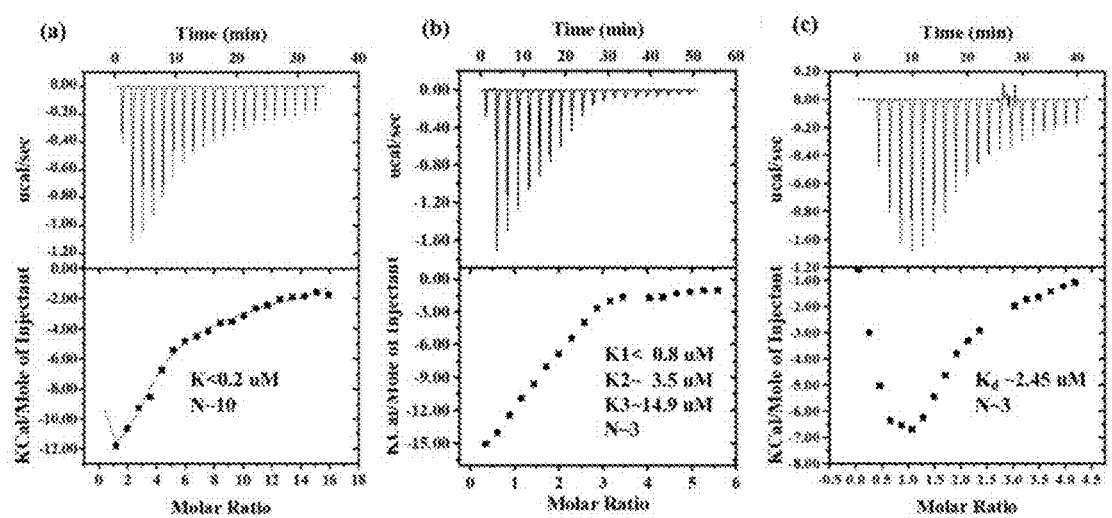
FIG. 3 shows the isothermal thermal titration (ITC) analysis of (a) Ag(I) (as AgNO$_3$), (b) Au(I) (as AuCl) and (c) Zn(II) (as zinc(II) acetate) binding to apo-MCR-1-S, respectively.

The apo-MCR-1-S without any tag was diluted into proper concentration for ITC assay. (1) 1 mM $Zn(Ac)_2$ was added into 30 μM apo-MCR-1-S; (2) 1.1 mM $AgNO_3$ were added into 7 μM apo-MCR-1-S; (3) 1.1 mM AuCl were added into 30 μM apo-MCR-1-S; (4) 1 mM other compounds were added into 30 μM apo-MCR-1-S. Negative groups were performed in dialysis buffer with or without 1% DMSO, depending on the special case. The stoichiometry of metal binding and binding affinities were obtained by fitting the data with proper equations and these assays were performed in triplicate. As shown in FIG. 3, The dissociation constants ($K_d$) were determined to be ca. 0.2 μM, 0.8 μM and 2.45 μM for the binding of MCR-1-S to $AgNO_3$, AuCl and $Zn(Ac)_2$, respectively. The corresponding data are shown in FIG. 3.

PAR Assay

Figure 4:
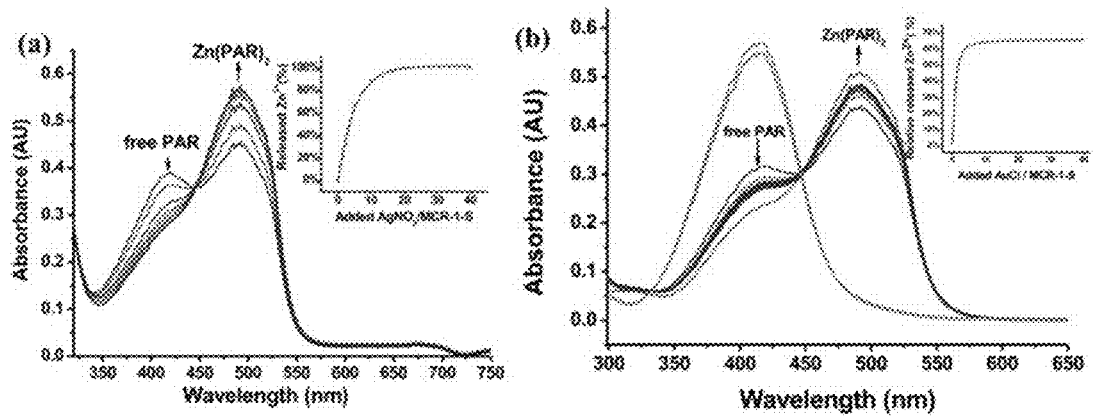
FIG. 4 shows the release of Zn(II) from Zn-MCR-1 by (a) Ag(I) (as AgNO$_3$), and (b) Au(I) (as AuCl) as revealed by 4-(2-pyridylazo) resorcinol (PAR) assay.

UV-visible spectra were collected by Varian Cary 50 spectrophotometer at a rate of 360 nm/min by using the 1 $cm^{-1}$ quartz cuvette. 4-(2-pyridylazo) resorcinol (PAR), a Zn(II) chelator, can strongly chelate free $Zn^{2+}$ to form $Zn(PAR)_2$ complex, leading to an obvious migration of maximum absorbance peak from ca. 420 nm to ca. 500 nm. Herein, we incubated apo-MCR-1-S with 10 folds $Zn^{2+}$ in dialysis buffer (20 mM HEPES, pH=7.4, 50 mM $NH_4NO_3$). After 12 hour incubation, Zn(II)-MCR-1-S was separated into aliquots and then mixed with Ag(I), Au(I) or even their compounds at different molecular ratios. Dialysis buffer instead of these metal compounds was added into Zn(II)-MCR-1-S solution as negative controls. For positive control, 10-folds of Zn(II) were mixed with apo-MCR-1-S. By comparing the peak intensities among different groups, the amounts of released Zn(II) could be calculated. UV-visible spectra were recorded in a range of 220-600 nm at least 30 min later after incubation. As shown in FIG. 4, the Zn(II) could be completely released from MCR-1-S upon the titration of Ag(I) and Au(I). The corresponding data are shown in FIG. 4.

Figure 5:
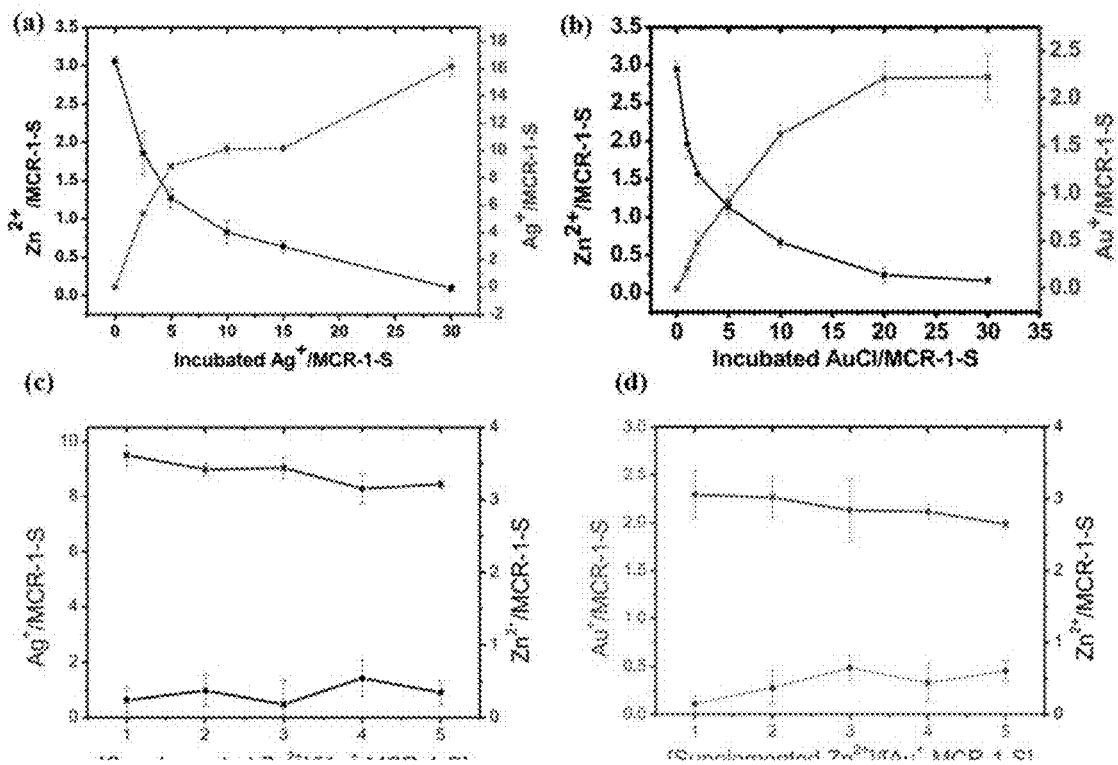
FIG. 5 (a-b) show the substitution of Zn(II) in MCR-1 by (a) AgNO$_3$, (b) AuCl as determined by ICP-MS. (c-d) show the activity of neither (c) Ag(I)-MCR-1-S or (d) Au(I) MCR-1-S can be restored by supplementation of Zn(II).

Metal content measurement and Zinc displacement analysis by ICP-MS To monitor the binding ratios of $Zn^{2+}$, $Au^+$ and $Ag^+$ to the protein, purified samples (native MCR-1-S and apo-MCR-1-S) were incubated with equivalents of $Zn^{2+}$, $Au^+$ or $Ag^+$ and then acidified by 65% $HNO_3$ (Sigma-Aldrich, USA) at 60° C. overnight. These acidified samples were diluted with 1% $HNO_3$ solution with $^{115}In$ (5 ppb) as an internal standard for corresponding metal ions, and then subjected to analysis by ICP-MS (Agilent 7500a, Agilent Technologies, CA, USA). Item 90243, 51844 and gold's standard (Fluka, Sigma-Aldrich, USA) were used as ICP standard samples. $^{34}S$ contents were also measured to further confirm protein concentration. The equilibrium dialysis was used to monitor the exact binding process. Apo-MCR-1-S was put in the inner side of dialysis membrane and outer side was supplemented with $Au^+$, $Ag^+$ or $Zn^{2+}$ at different molar ratios. $Zn^{2+}$ displacement analysis was performed by adding equivalents of $Au^+$ and $Ag^+$ into outer side of the membrane. It was found that about 3 molar equivalents of Zn(II) were replaced by 16 and 2.25 equivalent of Ag(I) and Au(I), respectively as determined from the respective metal contents of the samples (FIG. 5*a-b*), while the protein bound Ag(I) and Au(I) could not be replaced by extraneous Zn(II) (FIG. 5*c-d*).

TLC Plate Assay

Figure 6:
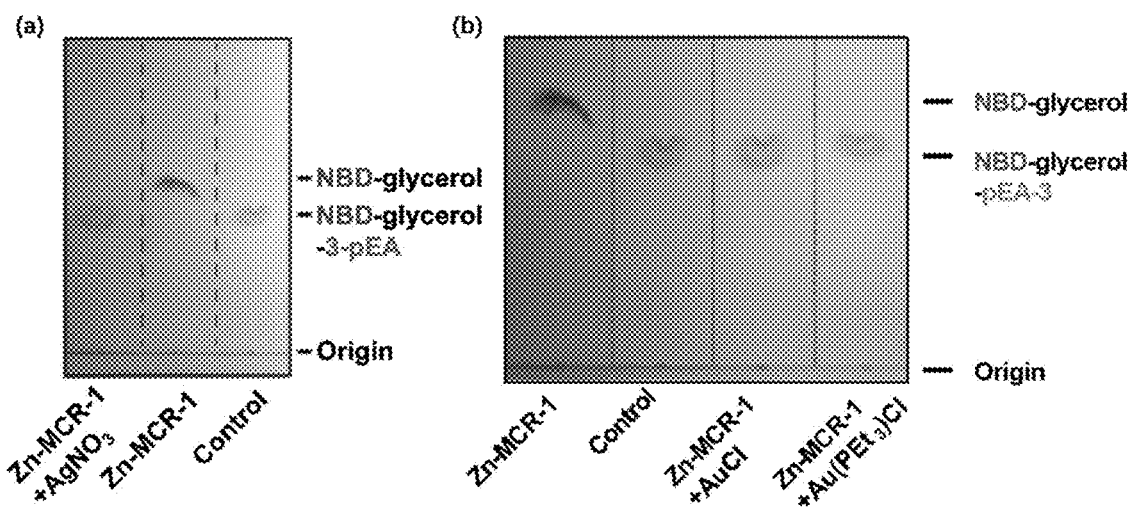
FIG. 6 shows the Inhibition of Zn-MCR-1 cleavage assay on NBD-glycerol-3-pEA by (a) AgNO$_3$ and (b) auranofin and Au(PEt$_3$)Cl, respectively. The representative images of TLC plate are shown here.

Inhibition of MCR-1 by $AgNO_3$ or auranofin was further assessed on a full-length protein by thin layer chromatography (TLC) plate assay. The full length MCR-1 was pre-treated with or without 10 molar equivalents of $AgNO_3$, AuCl and $Au(PEt_3)Cl$, respectively, and subsequently mixed with a fluorescent substrate NBD-glycerol-3-pEA (Avanti Lipids, USA) in assay buffer at 25° C. overnight. TLC plate was used to separate NBD-glycerol from the MCR-1 reaction mixture in a mobile phase [ethyl acetate:methanol: water, 7:2:1 (vol/vol)]. The reaction product was analyzed by exposing the TLC plate to UV light (455-485 nm) and visualizing the fluorescent signals with a gel imaging system. As shown in FIG. 6, native MCR-1 cleaved pEA group from NBD-glycerol-3-pEA, resulting in the faster migration of NBD-glycerol. In contrast, none of $AgNO_3$, AuCl or $Au(PEt_3)Cl$ treatment group exhibited observable migration, indicative of the inhibition of cleavage activity of MCR-1 by Ag(I) and Au(I).

Cellular Thermal Shift Assay

Figure 7:
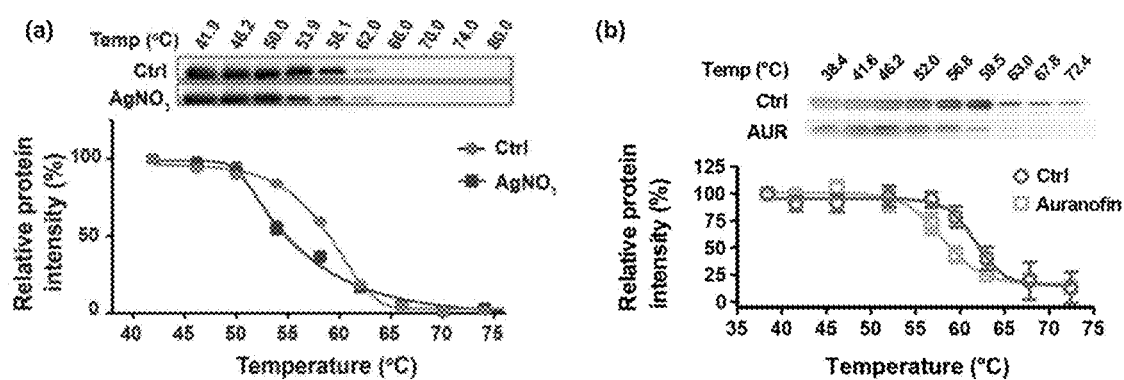
FIG. 7 shows (a) AgNO$_3$ and (b) auranofin engage with MCR-1 in bacterial cells by cellular thermal shift assay.

Considering that MCR-1 is a transmembrane protein, we constructed a plasmid with solvable truncated MCR-1 fragment (200-541 aa) but without any tag and then transferred it into *E. coli* BL21(DE3). The cellular thermal shift assay was performed according to a general standard method. Bacterial cultures at logarithmic phase were exposed to treatment of 1 μg $mL^{-1}$ $AgNO_3$, 1 μg $mL^{-1}$ and 15 μg $mL^{-1}$ auranofin, respectively overnight. The bacterial pellets were harvested and washed with PBS for 3 times. The cell suspensions were aliquoted into PCR tubes and heat treatment was performed at the designated temperature for 3 mins in a 96-well thermal cycler. The tubes were cooled immediately at 25° C., and the heat treatments were repeated for three cycles. For the cell lysis, the samples were frozen-thawed in liquid nitrogen and thermal cycler was set at 25° C. The samples were vortexed gently after each cycle and centrifuged at 20,000×g to obtain the supernatant. All the samples were subjected to SDS-PAGE gel and electrotransferred to a PVDF membrane (Hybond-P, GE Healthcare). A PageRuler Prestained Protein Ladder #26616 (Thermo) was used as a standard marker. Diluted protein primary antibody (MCR-1 polyclonal antibody (CSB-PA745804LA01 ENL, Cusabio Technology LLC) and the secondary antibody (Anti-rabbit IgG, HRP-linked Antibody, #7074, Cell Signaling Technology, Inc.) were applied after the standard blotting procedures. The protein bands were colorimetrically developed with specified ratio of substrates comprising nitroblue tetrazolium/5-bromo-4-chloro-3-indolyl phosphate (NBT/BCIP) for 15 mins. Signal of each band was quantified the for analysis. As shown in FIG. 7, overnight exposure to $AgNO_3$ and auranofin treatment decreased the cellular thermal stability of MCR-1 by $\Delta T_m$=5.4° C. and 5.2° C., respectively, in cellulo, indicative of the binding of $AgNO_3$ or auranofin to MCR-1 in intact cells.

Membrane Potential Assay

Figure 8:
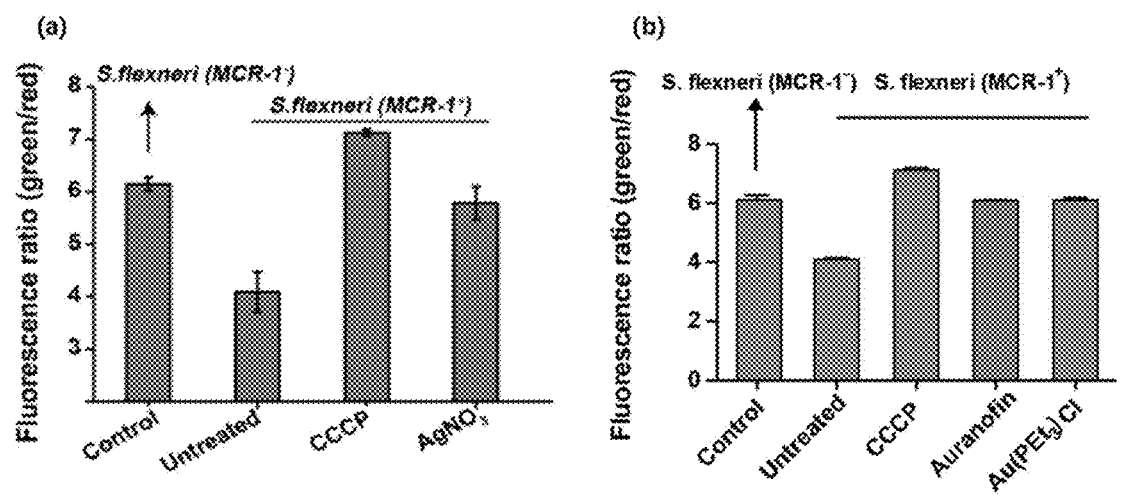
FIG. 8 shows membrane potential changes upon the treatment of (a) AgNO$_3$ and (b) auranofinin or Au(PEt$_3$)Cl in MCR-1 positive and negative S. flexneri, respectively, as determined by the ratios of green to red fluorescent signals.

MCR-1 is organized into two domains including an N-terminal inner membrane-bound domain and a soluble, periplasmic domain equipped with a Zn-dependent catalytic core and two (putative) substrate-binding pockets. This enzyme could bind PEA and lipid A in respective pockets and launch the Zn-dependent transfer of PEA to lipid A with the assistance of its transmembrane domain. Membrane potential assay was carried out based on a modified method according to manufacturer's instructions. Briefly, about $10^6$ CFU mid-log phase bacterial pellets (S. flexneri (MCR-1$^+$) or S. flexneri (MCR-1$^-$)) that were preincubated with AgNO$_3$ (10 µM), auranofin (3 µM), Au(PEt$_3$)Cl (3 µM) or CCCP (5 µM), respectively and then washed with PBS for 3 times. The bacterial pellets were then resuspended in PBS supplemented with DiOC2 (30 µM) and stained at 37° C. for 30 mins. Stained bacteria were then assayed in a flow cytometer and the signals from FITC-A (488 nm, green gate) and PI-A (633 nm, red gate) were collected and then analyzed. S. flexneri without treatment served as the control. As shown in FIG. 8, green/red fluorescent ratios decreased from 6.1 to 4.1, indicative of the significant reduction of the membrane negative charge in MCR-1 positive S. flexneri in comparison to the MCR-1 negative strain. Treatment of MCR-1 positive S. flexneri with AgNO$_3$, auranofin or Au(PEt$_3$)Cl led to the significant recovery of fluorescence ratio to 5.8, 6.1, 6.1 and 7.1, respectively, which were the levels found for the negative control. This demonstrated that Ag(I) and Au(I) effectively prevents the MCR-1-induced loss of negative charges in cellulo.

Example 3: In Vitro Antimicrobial Activity Assessment

The antimicrobial activity of silver/gold was examined against MCR-producing bacterial strains. The method involved cell-based minimum inhibitory concentration assay, time-kill assay and in vitro cell infection assay.

Bacteria

The bacteria employed involved E. coli J53, E. coli DH5a, E. coli BL-21, E. coli clinical isolate 1493, clinical isolates of Salmonella enterica, Salmonella typhimurium, Klebsiella pneumoniae, Shigella flexneri, Enterobacter aerogenes, Enterobacter asburiae, Enterobacter kobei.

Microdilution MIC Assay

MIC values of either antibiotics or Bi(III) compounds were determined firstly by standard broth micro-dilution method (Clinical and Laboratory Standards Institute (CLSI) M100-S20, 2010). Briefly, bacteria cells were cultured in LB broth overnight at 37° C. at 250 rpm and the optical density was measured at 600 nm (OD$_{600}$) using a microtiter plate reader. The bacterial density was adjusted to about $1 \times 10^6$ CFU mL$^{-1}$ and checked by CFU counting on agar plates afterwards. Tested compounds were added triplicately into individual wells of flat-bottomed 96-well plates and performed two-fold serial dilution, followed by addition of prepared bacterial inoculum. The plate was then incubated at 37° C. overnight. Lanes with no antibiotics or bismuth compounds served as positive controls and lanes with no bacteria added served as negative controls. The MIC was determined as the lowest concentration of compounds that could inhibit the growth of microorganism by both visual reading and OD$_{600}$ measurement.

For the test of drug combination, antibiotics and Bi(III) compounds were co-administrated at concentrations up to 8 times higher than the MIC of the compounds tested alone. Other procedures and the check of MIC were kept strictly the same. The FICIs were determined based on the following equation:

$$FICI = FIC_A + FIC_B = C_A/MIC_A + C_B/MIC_B$$

where $MIC_A$ and $MIC_B$ are the MIC values of compound A and B when functioning alone, and $C_A$ and $C_B$ are the concentrations of compound A and B at the effective combinations. Synergism was defined as FICI≤0.5, indifference was defined as FICI>0.5 and <4, and antagonism was defined as FICI≥4. All of the determinations were performed at least in triplicate on different days.

Figure 9:
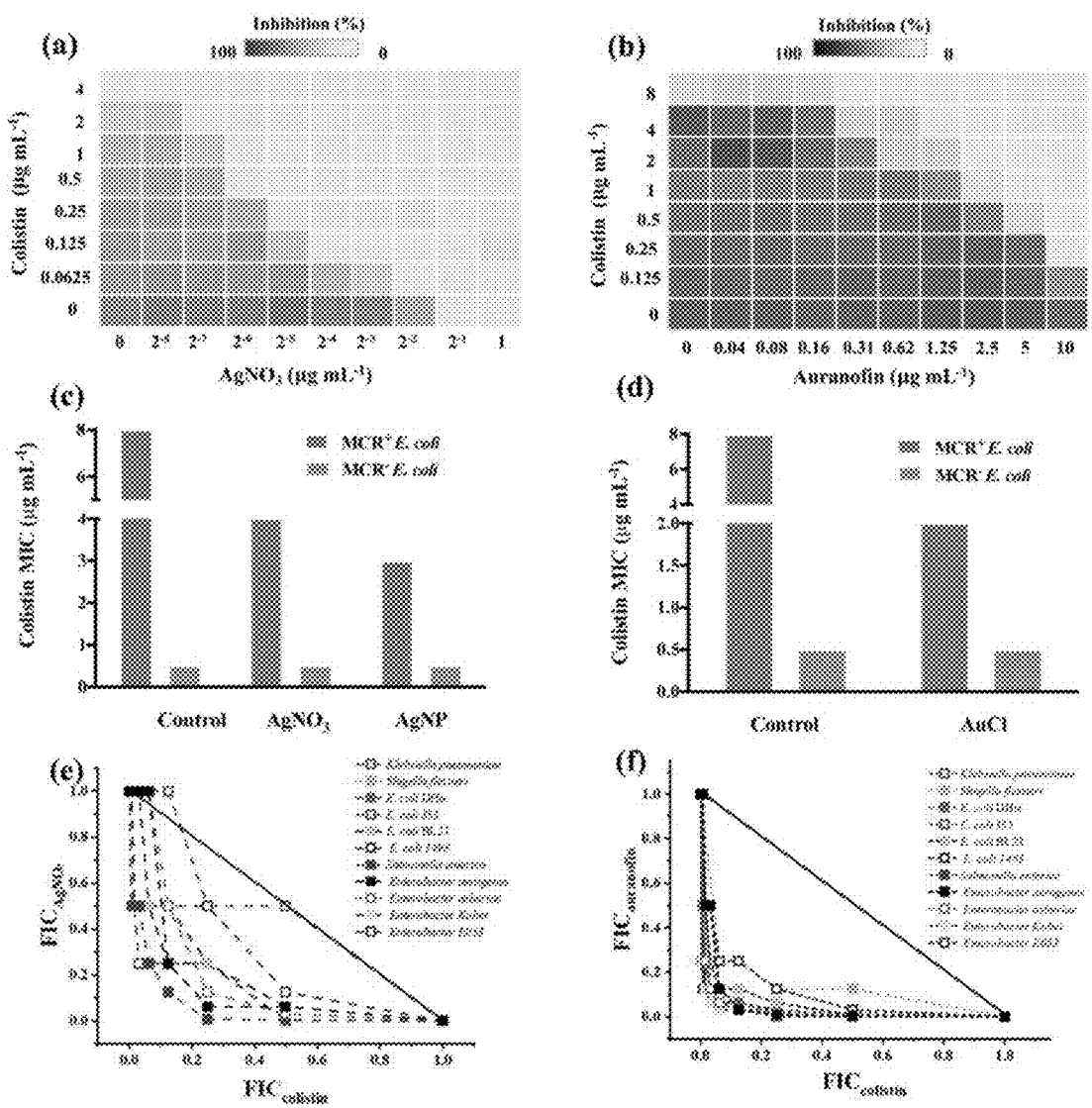
FIG. 9 (a-b) show a heat map of checkerboard MIC analysis over colistin and (a) silver nitrate or (b) auranofin against clinical isolates of MCR-1-producing bacteria. (c-d) show colistin MIC in the absence or presence of (c) AgNO$_3$, AgNP or (d) AuCl against MCR-positive or negative *E. coli*. (e-f) show isobolic curves of combination therapies between colistin and (c) AgNO$_3$ and (d) AuCl against MCR-1-producing bacterial strains.

Using the methods described above, exemplary silver/gold compounds were evaluated for their ability to kill or inhibit the growth of MCR-producing bacteria in the combination with colistin. FIG. 9a-d show the heat map of checkerboard MIC on the combination of colistin and AgNO$_3$ against MCR-producing E. coli. When used alone, colistin had relatively high MIC values, often greater than 4 µg mL$^{-1}$, which are beyond the empirical susceptible level for Enterobacteriaceae (2 µg mL$^{-1}$). As the concentration of AgNO$_3$ increased, MIC of colistin was gradually lowed to 0.0625 µg mL$^{-1}$ and FIC index was calculated to be 0.125, indicative of synergistic effect between them. Similarly, auranofin was able to decrease colistin MIC to 0.25 µg mL$^{-1}$ with FICI of 0.375. In contrast, no inhibition was observed when MCR-1-negative E. coli stain was used. Such a synergy was also found for other exemplary silver/gold compounds against MCR-1-producing bacterial strains (FIG. 9e-f). Upon the combination with tested silver/gold compounds, colistin MICs were substantially lowered, typically by 2~64 folds against MCR-producing bacteria. Similar synergistic patterns could be also observed in MCR-1 variants or other MCR variants (FIG. 9).

Time Kill Assay

Figure 10:
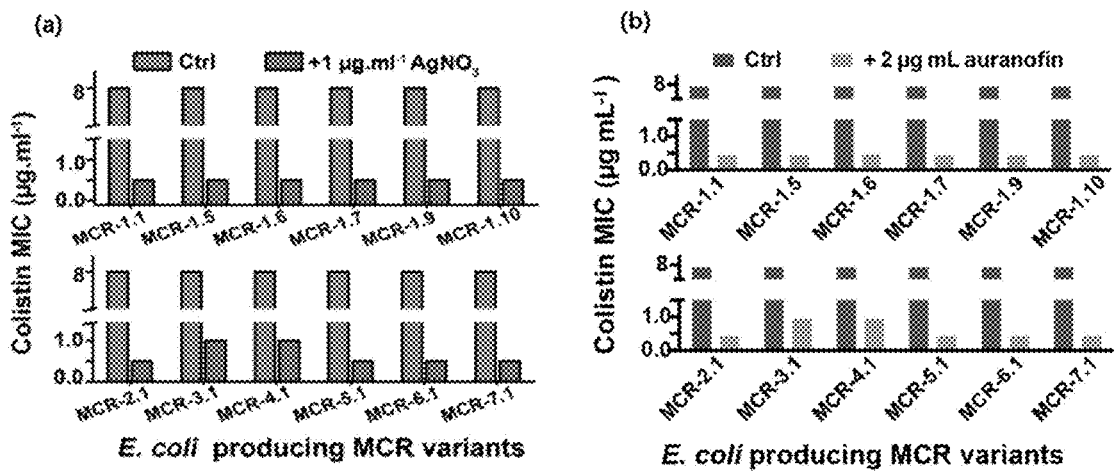
FIG. 10 shows time-kill curves at log-phase for MCR-1-positive *E. coli* upon treatment of (a) vehicle, colistin, AgNO$_3$, or their combination and (b) vehicle, colistin, auranofin or their combination, for up to 24 hours.
Figure 11:
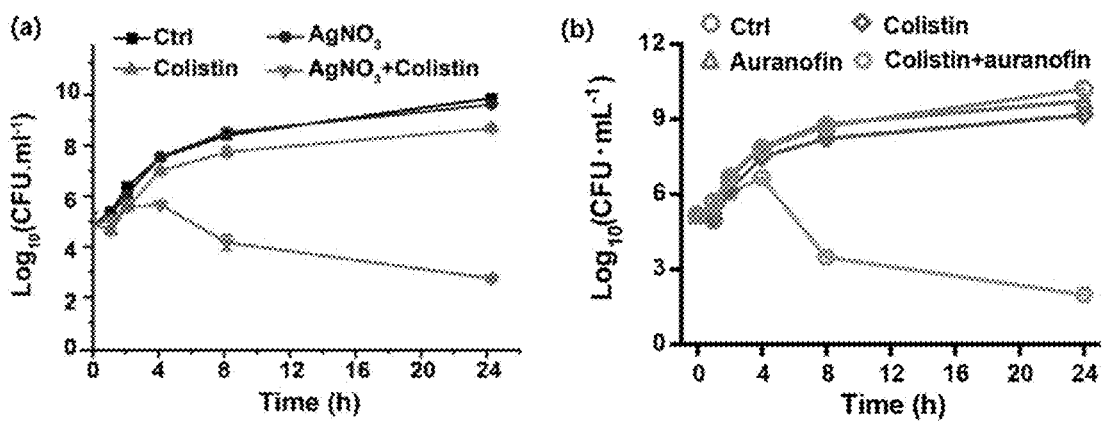
FIG. 11 reveals the reduction of COL MIC for *E. coli* J53 that produced MCR-1 variants and MCR homologs in the combined use with (a) AgNO$_3$ and (b) auranofin, respectively.

Time kill assay was used to further explore the synergy between MCR and silver/gold compounds which were represented by AgNO$_3$ and auranofin herein. In a typical assay, the concentrations of the compounds used in this test represent as follows: 2 µg mL$^{-1}$ colistin, 10 µg mL$^{-1}$ AgNO$_3$ or 6 µg mL$^{-1}$ auranofin. MCR-producing E. coli were cultured at 37° C. overnight and diluted 1:250 into LB broth for 3 hrs to reach log phase. The initial bacterial concentration was adjusted to ~$10^7$ CFU mL$^{-1}$ according to standard curve. Tested compounds either alone or in combination were added to 20 mL of freshly prepared bacterial solution in a 50 mL tube, and incubate at 37° C. LB broth with no compounds served as a positive control. Aliquots of 100 mL suspension were withdrawn after different time intervals (0, 1, 2, 4, 6, 8, and 24 hours). Bacterial concentrations were estimated from colony counts by serial dilution in phosphate-buffered saline (PBS) and plating on LB agar. All assays were triplicated and performed three times in different days. Data from three independent experiments were averaged and plotted as log$_{10}$ CFU mL$^{-1}$ versus time (h) for each time point over 24 hrs as shown in FIG. 10.

In comparison to single components, bacterial density was significantly lowered by more than 10000 folds when exposed to the compound combination of colistin and AgNO$_3$ or auranofin at the endpoint of the assay. According to NCCLS, this indicates an evident synergism between colistin and AgNO$_3$ or auranofin, and the bactericidal effect over the compound combination was observed as well.

Resistance Study

Given the very notion of MIC, all susceptible bacterial cells are suppressed or killed by a dose above it. However, bacterial population is often large; an infection likely contains first-step mutants with lower susceptibility. The dose of compounds at MIC adversely amplifies the population of those less-susceptible mutants. Thus, mutant prevention concentration (MPC), defined as a compound concentration that suppresses the growth of first-step resistant mutant in large quantity of susceptible bacterial population, together with mutant prevention index (MPI=MPC/MIC), is introduced to estimate the mutant prevention ability of exemplary compound combination. For a typical test, MCR-1-producing E. coli cells at 1~2×10$^{10}$ CFU were spread onto LB agar containing combinations of colistin and AgNO$_3$ or auranofin at identical concentrations. All the plates were incubated at 37° C. Upon incubation for 48 hours, up to 4 colonies were picked and re-cultured from any plates with observable colonies, followed by the measurement of their MIC values. Any MICs of colistin that were higher than the original values (4 μg mL$^{-1}$) were determined as mutant colony. The concentration that restricted the growth of mutant colonies was determined as MPC.

As shown in the bar charts (FIG. 12a), mutant colonies were still observable even when a high dose (16×MIC) of colistin was applied alone. In contrast, with the increase in AgNO$_3$ or auranofin, the mutation frequency significantly declined. The MPI of colistin was lowered to 0.5 and no mutant colony was observable when 30 μg mL$^{-1}$ AgNO$_3$ or auranofin, was applied, respectively.

Figure 12:
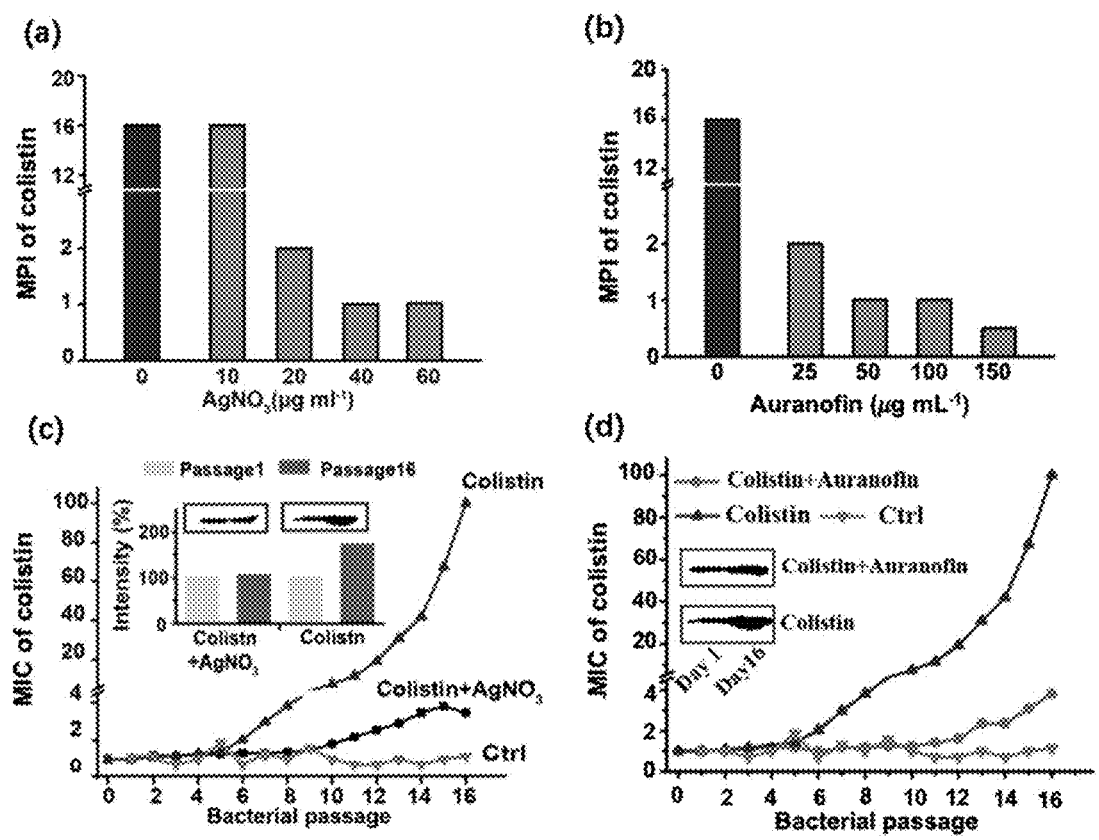
FIG. 12 (a-b) shows mutation prevention concentration of colistin in the presence of (a) AgNO$_3$ and (b) auranofin against MCR-1-producing *E. coli*. (c-d) shows resistance acquisition curves during serial passage in MCR-1 producing *E. coli* with the subinhibitory concentration of colistin or its combination at identical concentration of (c) AgNO$_3$ and (d) auranofin, respectively. Insets shows the normalized expression levels of MCR-1 after serial passage.

The in vitro passage assay was also conducted to evaluate the antimicrobial durability of the combination. In a typical experiment, an overnight culture of MCR-producing E. coli was diluted to 10$^7$ CFU mL$^{-1}$ in LB broth. The as-diluted bacterial suspension was added to each well of 96-well plate supplemented with the drug at 0.5-fold, 0.75-fold, 1-fold, 1.25-fold, 1.5-fold, 1.75-fold, 2-fold, 3-fold, and 4-fold MIC, respectively. The drug concentrations for in vitro selection were increased to 2-fold, 4-fold, 6-fold, 8-fold, 16-fold, 24-fold, and 32-fold of MIC, respectively, after 10 bacterial passages. All the plates were incubated at 37° C. and the growth of cultures was checked at 24 h intervals. Cultures from the second highest concentrations that allowed growth were performed 1:1000 dilution into fresh medium supplemented with the same concentrations of drugs. For colistin, 1-fold of MIC was set as 4 μg mL$^{-1}$. This in vitro passage was repeated for 20 days. MIC of MER was determined every four passages. After 16 serial passages, the MIC of colistin alone group was raised by 16 folds while the combined use of AgNO$_3$ or auranofin slowed down the resistance development with MIC increased by 4 folds (FIG. 12b).

In Vitro Cell Infection Assay

Figure 13:
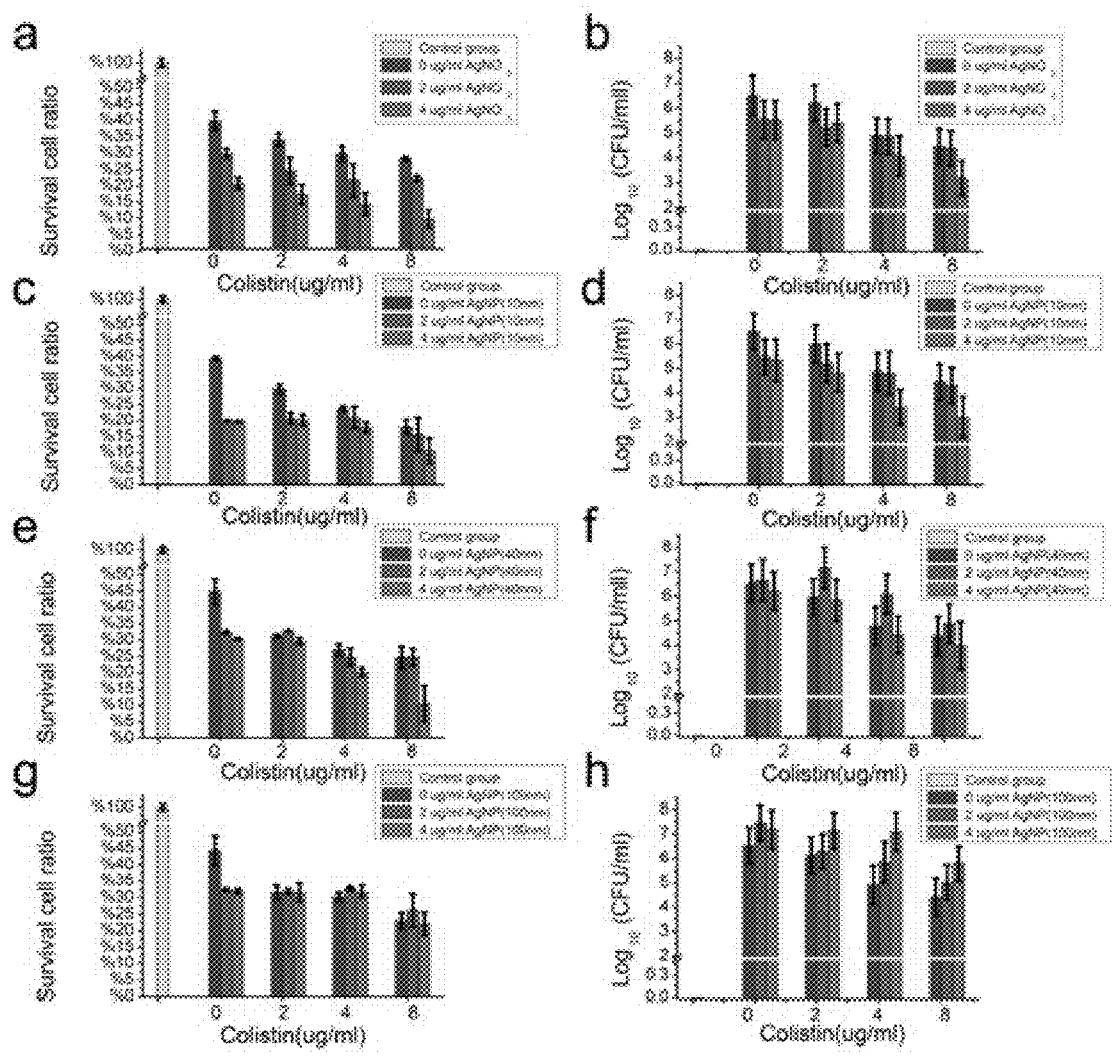
FIG. 13 (a)-(h) show the bacterial density and cell viability after exposure of colistin in combination with (a-b) AgNO$_3$ or (c-h) AgNPs with different sizes in cell-invaded model.

HepG2 cells were cultured in dulbecco's modified eagle medium (DMEM) supplemented with fetal bovine serum (FBS, 10%) and grown at 37° C. in the 5% CO$_2$ humidified atmosphere for three days. The cells were then washed three times with phosphate buffer saline (PBS) solution, liberated with trypsin-EDTA (0.25%) and re-suspended by culture medium. About 500 μL of re-suspended cells (about 5.0× 10$^4$) were seeded in 96-well plates and incubated as described above for 48 hours to ensure its confluency. The fresh logarithmic MCR-1-producing Shigella flexneri, were washed with PBS for three times and re-suspended in MEM/10% FBS. The density was adjusted to 1.0×10$^7$ CFU mL$^{-1}$. Then 25 μL of bacterial suspension were added to each well and substituted for the previous cell culture medium. The plates were centrifuged at 800 g for 10 min and then incubated at 37° C. in 5% CO$_2$ for 6 hours executing the bacterial invasion at multiplicity of infection (MOI) of 5. We herein then used cell-associated bacterial infection model where the cell-associated bacteria are defined as bacteria that attach to, penetrate, or transcytose in HepG2 cells. After the infection, cells were washed with PBS for six times to remove unbound bacteria. The infected HepG2 cells were then exposed to either colistin or AgNO$_3$/AgNPs compounds, or their combination overnight under identical cell culture condition. Cells in the absence of drugs served as a control. The bacterial loads were examined by lysing HepG2 cells with 1% Triton X-100 in PBS and serially diluting the resulting lysates to enumerate bacterial colonies by agar plating. Those cells grown under culture medium alone were used as a negative control. After the fixed incubation duration, 50 μL of XTT labeling mixture were added to each well, and the cells were incubated for 2 hours at 37° C. under a humidified atmosphere of 5% CO$_2$. The formation of formazan dyes, produced only by metabolic active cells, was detected spectrophotometrically at 490 nm. Surviving bacteria were enumerated as described previously. The assay was performed in triplicate, repeated three times, and results were expressed as average±SD. FIG. 13 shows the more than 100-fold decrease in bacterial loads was observed for combination group in comparison to colistin alone or 1000-fold decrease in comparison to control group. The HepG2 cell survival rate was evaluated by the XTT assay, and silver nitrate did not exhibit or showed very low cytotoxicity against HepG2 cells even at the highest dose. The above studies demonstrate the in vitro potency of the combination of colistin and AgNO$_3$ against MCR-1-producing bacteria while showing low cytotoxicity to mammalian cells.

In Vivo Murine Infection Model

Figure 14:
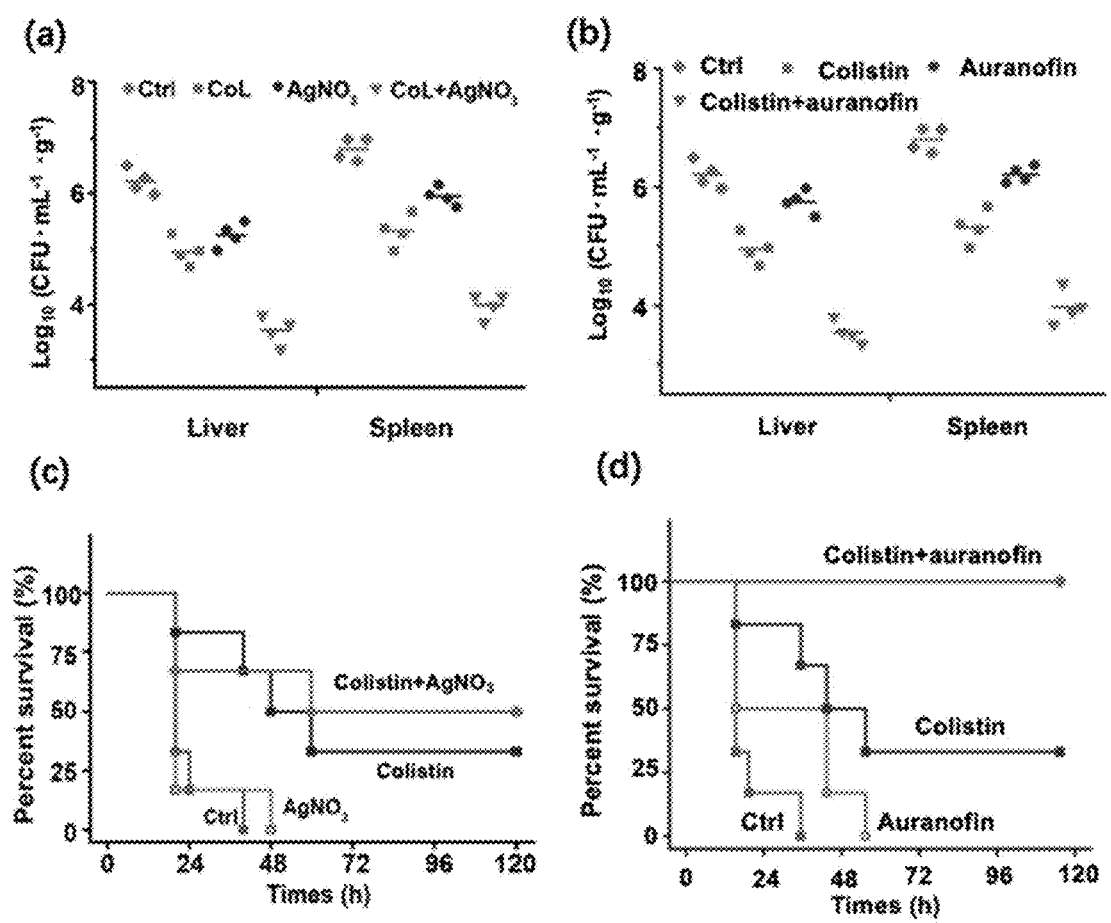
FIG. 14 (a-b) show bacterial loads in the liver and spleen from Balb/c mice infected by a sub-lethal dose of *K. pneumoniae* 9607 (MCR-1+). Groups of infected mice received single dose of i.p. administration of (a) vehicle, AgNO$_3$, colistin or their combination, and (c-d) vehicle, auranofin, colistin or their combination, respectively.

The in vivo antimicrobial efficacy of the combination of colistin and AgNO$_3$ or auranofin were further examined by a local or systemic infection model. For local infection experiment, an overnight culture of K. pneumoniae 9607 (MCR-1$^+$) was performed 1:250 dilution in LB broth and re-grew to about OD$_{600}$ 0.5 at 37° C., 250 rpm. Bacterial pellets were collected and washed by PBS buffer three times for further use. Mice were infected intraperitoneally (i.p.) with a dose of 2×10$^6$ CFU of bacteria in PBS. Four groups of mice were i.p. administered 1-hr post-infection with single dose of vehicle, colistin (2 mg kg$^{-1}$), auranofin (0.5 mg kg$^{-1}$), AgNO3 (1.5 mg kg$^{-1}$) or their combination therapy. All the mice were scarified at 48 hrs following systemic infection, and bacterial loads in livers and spleens were examined by agar plating. For survival assay, all the operations of infection were similar, except that infection was induced by E. coli CKE at 5×10$^6$ CFU per mice in the presence of 2% mucin, and single dose of vehicle, colistin (1 mg·kg$^{-1}$), AgNO3 (0.75 mg kg$^{-1}$) auranofin (0.25 mg·kg$^{-1}$), or their combination, was i.p. injected to the infected mice 0.5-hr post infection. Body weights and mice survival were monitored till endpoint of the experiment. As shown in FIG. 14a-b, in comparison to the CFUs (at 10$^5$ cfu mL$^{-1}$ g$^{-1}$ level) in both liver and spleen of mice treated by either colistin, AgNO$_3$ or auranofin monotherapy, a significant reduction by >20-fold in the CFUs were observed in either AgNO$_3$— or auranofin-based combination therapy. In the systemic infection model, our result (FIG. 14c-d) showed that AgNO$_3$ or auranofin mono-therapy failed to protect any of the mice from death within 72 hours, and colistin mono-therapy led to only 30% mice survival within the period examined. However, the AgNO$_3$-based combination therapy effectively postponed the death of mice and led to half of the mice being rescued (3 out of 6 mice) and auranofin-based therapy served to protect all the infected mice from death. Collectively, we demonstrate that in vitro antimicrobial efficacy of AgNO$_3$ and colistin combination therapy could be well translated into in vivo efficacy.

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about."

While the invention is explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A pharmaceutical composition, comprising:
   at least one polymyxin antibiotic comprising at least one of colistin A or colistin B; and
   at least one mobile colistin resistant proteins inhibitor comprising a silver compound,
   wherein a molar ratio of the at least one polymyxin antibiotic to the at least one mobile colistin resistant proteins inhibitor is from 16:1 to 64:1 by weight (w/w).

2. The pharmaceutical composition according to claim 1, wherein the at least one mobile colistin resistant proteins inhibitor further comprises a gold compound.

3. A method for treating a mobile colistin resistant proteins inhibitor producing bacterial infection, comprising:
   administering to a patient in need thereof an effective amount of the pharmaceutical composition of claim 1.

4. A method of making a pharmaceutical composition, comprising:
   combining at least one polymyxin antibiotic, comprising at least one of colistin A or colistin B, and at least one mobile colistin resistant proteins inhibitor, comprising a silver compound, in a molar ratio of the at least one polymyxin antibiotic to the at least one mobile colistin resistant proteins inhibitor from 16:1 to 64:1.

5. The method of making a pharmaceutical composition according to claim 4, wherein the at least one mobile colistin resistant proteins inhibitor further comprises a gold compound.

6. The method of making a pharmaceutical composition according to claim 4, wherein the molar ratio of the at least one polymyxin antibiotic to the at least one mobile colistin resistant proteins inhibitor is from 25:1 to 50:1.

7. The pharmaceutical composition according to claim 1, wherein the molar ratio of the at least one polymyxin antibiotic to the at least one mobile colistin resistant proteins inhibitor is from 25:1 to 50:1.

8. The method for treating a mobile colistin resistant proteins inhibitor producing bacterial infection according to claim 3, wherein the at least one mobile colistin resistant proteins inhibitor further comprises a gold compound.

9. The method for treating a mobile colistin resistant proteins inhibitor producing bacterial infection according to claim 3, wherein the molar ratio of the at least one polymyxin antibiotic to the at least one mobile colistin resistant proteins inhibitor is from 25:1 to 50:1.

* * * * *